US012703672B2

(12) United States Patent
Lu et al.

(10) Patent No.: US 12,703,672 B2
(45) Date of Patent: Aug. 11, 2026

(54) INDUSTRIAL EXTRACTION METHOD OF CANNABIDIOL

(71) Applicant: CHENGUANG BIOTECH GROUP CO., LTD., Hebei (CN)

(72) Inventors: Qingguo Lu, Hebei (CN); Yunhe Lian, Hebei (CN); Wei Gao, Hebei (CN); Yang Li, Hebei (CN); Hong Tian, Hebei (CN)

(73) Assignee: CHENGUANG BIOTECH GROUP CO., LTD., Hebei (CN)

( * ) Notice: Subject to any disclaimer, the term of this patent is extended or adjusted under 35 U.S.C. 154(b) by 908 days.

(21) Appl. No.: 18/002,078

(22) PCT Filed: May 27, 2021

(86) PCT No.: PCT/CN2021/096338
§ 371 (c)(1),
(2) Date: Dec. 16, 2022

(87) PCT Pub. No.: WO2021/254121
PCT Pub. Date: Dec. 23, 2021

(65) Prior Publication Data

US 2023/0219872 A1 Jul. 13, 2023

(30) Foreign Application Priority Data

Jun. 16, 2020 (CN) ........................ 202010546109.0

(51) Int. Cl.
*C07C 37/82* (2006.01)

(52) U.S. Cl.
CPC .......... *C07C 37/82* (2013.01); *C07C 2601/16* (2017.05)

(58) Field of Classification Search
CPC ...... C07C 37/72; C07C 37/82; C07C 2601/16
See application file for complete search history.

(56) References Cited

U.S. PATENT DOCUMENTS 10,301,242 B2 * 5/2019 Zhang ..................... C07C 37/84

FOREIGN PATENT DOCUMENTS

| | | |
|---|---|---|
| CN | 105535111 A | 5/2016 |
| CN | 106831353 A | 6/2017 |
| CN | 109988060 A | 7/2019 |
| CN | 110256206 A | 9/2019 |
| CN | 110283048 A | 9/2019 |
| CN | 110655453 A | 1/2020 |
| CN | 111099970 A | 5/2020 |

OTHER PUBLICATIONS

International Search Report and Written Opinion for corresponding International application No. PCT/CN2021/096338; dated Aug. 27, 2021 (10 pages) Machine Translation.

* cited by examiner

*Primary Examiner* — Sikarl A Witherspoon
(74) *Attorney, Agent, or Firm* — Mendelsohn Dunleavy, PC; Kevin J. Dunleavy

(57) ABSTRACT

Disclosed is an industrial extraction method of cannabidiol, pertaining to the field of medicine and chemical industry. The present invention aims to resolve the problems of difficulty in wax removal, low extraction rate of cannabidiol, and excessively high content of tetrahydrocannabinol during extraction using conventional solvents in the prior art. The extraction method employs raw material pretreatment, granulation, extraction, liquid-liquid extraction, decolorization, concentration, and other processes, such that wax removal from an extracted liquid is improved, the purity of a crude cannabidiol oil can be increased to 60%, and 40% of tetrahydrocannabinol can be removed. The method has high extraction yields and low costs, and can be implemented in large-scale industrial production.

20 Claims, No Drawings

INDUSTRIAL EXTRACTION METHOD OF CANNABIDIOL

CROSS-REFERENCE TO RELATED APPLICATION

The present application claims priority to Chinese Patent Application No. 202010546109.0, entitled "Industrial extraction method of cannabidiol", and filed on Jun. 16, 2020, the entire disclosure of which is incorporated herein by reference in its entirety.

TECHNICAL FIELD

The present invention relates to the technical field of cannabidiol preparation and, in particular, to an industrial extraction method of cannabidiol.

BACKGROUND ART

Cannabidiol (abbreviated as CBD), which is extracted from female cannabis plants, is the main chemical component of the medicinal plant cannabis, and is a non-addictive component of cannabis with pharmacological effects such as anti-spasm, anti-anxiety, and anti-inflammatory.

Tetrahydrocannabinol (abbreviated as THC) is the main active ingredient in cannabis-based drugs, and has psycho- and medically active effects when sucked or taken orally. Large amounts or long-term use can cause serious damage to a person's health.

Since THC is a prohibited ingredient, it must be removed during the preparation of cannabidiol. If most of the tetrahydrocannabinol is removed before the refinement of cannabidiol, the subsequent operation steps of separation and refinement can be reduced, and the cost for separation and refinement can be significantly reduced. Currently, cannabidiol is mostly obtained by extraction and separation from the plant cannabis, in the preliminary extraction process, the extract will inevitably be mixed with tetrahydrocannabinol and other impurities, such as waxes. The presence of waxes will affect the physical and chemical properties of the extract, which in turn affects the subsequent refining steps of cannabidiol, such as affecting the elution efficiency in the subsequent column chromatography separation, reducing the yield of cannabidiol.

The current preparation technology of cannabidiol is not highly applied in the industrial field, and is not enough to form large-scale production. Using conventional solvent extraction, it is inevitable to extract the waxy components from raw materials, further, the subsequent use of winterization treatment, although some of the wax can be removed, but the removal effect is poor, and the cost is high.

In Patent No. 201610087327.6, it discloses a hemp extract rich in cannabidiol from the leaves and leaves of industrial hemp and its preparation method. Subcritical butane extraction technology is used in the patent to extract the crude extract, and then the extract was dissolved with ethanol, and the resultant was subjected to low-temperature winterization treatment, and the wax was removed by centrifugation. The patent process is complicated, and can not completely remove the wax.

Existing patent application Nos. CN110655453A and CN110256206A describe that hemp is extracted by methanol or ethanol, after the alcohol extract obtained is concentrated, hexane or petroleum ether is further added for extraction to obtain an organic layer, and an intermediate product of hemp extract is obtained after recovery of organic solvent. This hemp extraction process is contrary to the extraction solvent and liquid-liquid extraction solvent used in the present application, which obtained a higher extraction rate of cannabidiol and reduced the content of tetrahydrocannabinol in the extract compared to the above process, and achieved better technical results.

Through the selection of extraction solvent and extractant, this patent uses the liquid-liquid extraction process to effectively separate the waxy components and cannabidiol, while improving the extraction rate of cannabidiol and remove 40% of tetrahydrocannabinol in the extract, which can greatly reduce the pressure of further chromatographic separation of CBD and THC, and provide convenience for the subsequent production process.

SUMMARY OF THE INVENTION

In order to solve the problems in the prior art that when conventional solvent extraction is used, the wax is not easily removed, or the removal cost is high, the extraction rate of cannabidiol is low, the tetrahydrocannabinol cannot be effectively removed, and the industrialized, low-cost and large-scale production cannot be realized, the present invention provides, in particular, an industrial extraction method of cannabidiol.

The specific steps of the industrial extraction method of cannabidiol include:

step one, crushing the hemp flowers and leaves and subjecting the resultant to heating and tossing or drying treatment at 100-150° C.;

step two, subjecting the hemp flowers and leaves after the treatment of drying in step one to solvent extraction, and concentrating the resulted extract solution to a certain amount remained;

step three, adding other solvents into the concentrated solution obtained after treatment of step two for liquid-liquid extraction;

step four, separating the resulted lower liquid after the treatment of step three, and adding activated carbon for stirring to decolorize; and step five, concentrating the decolorized liquid obtained after treatment of step four, and deodorizing to obtain a cannabidiol-rich oil paste.

In step one of the method for industrial extraction of cannabidiol, the heating or drying temperature is preferably 120-140° C.; further preferably 125-135° C.; most preferably 130° C.; crushing to 10-30 mesh; further preferably 15-25 mesh; most preferably 20 mesh.

In step two of the method for industrial extraction of cannabidiol, the hemp flowers and leaves are granulated and then extracted.

In step two of the method for industrial extraction of cannabidiol, the extraction solvent is organic solvent selected from hexane, cyclohexane, n-heptane, petroleum ether, vegetable oil extraction solvent, ethyl acetate, butyl acetate and the like, and the mass/volume ratio (g/mL) of the hemp flowers and leaves to the extraction solvent is 1:4 to 1:8.

In step two of the method for industrial extraction of cannabidiol, the extraction solution is concentrated to 1/15 to 1/5; preferably 1/12 to 1/8; and most preferably 1/10 of the original solvent volume.

In step two of the method for industrial extraction of cannabidiol, the extraction solvent is preferably selected from hexane, petroleum ether and vegetable oil extraction solvent.

In step three of the method for industrial extraction of cannabidiol, the liquid-liquid extraction solvent used is solvent selected from methanol, ethanol, pentanol, butanol, isopropanol and the like, the volume ratio of the concentrated solution to the liquid-liquid extraction solvent is 1:2 to 1:6, after the extraction solvent is added, the obtained solution is stirred for 10 min to 30 min and left standing for 60 min to 120 min, so that the two phases of the solvent are completely separated.

In step three of the method for industrial extraction of cannabidiol, the extractant used is preferably selected from 60%-75% of methanol, ethanol, pentanol, butanol and isopropanol; furthermore, the extractant is preferably 60%-75% of methanol or ethanol.

In step four of the method for industrial extraction of cannabidiol, the amount of the activated carbon added is 0.1%-3% (g/ml) of the lower layer liquid.

In step four of the method for industrial extraction of cannabidiol, the activated carbon is woody porous activated carbon and the treatment time is 5-10 minutes.

A preferred method for industrial extraction of cannabidiol is also provided by the present application, which is characterized by the following steps:

step one, crushing the hemp flowers and leaves to 10-30 mesh and subjecting the resultant to heating and tossing or drying treatment at 120-140° C.;

step two, subjecting the hemp flowers and leaves after the treatment of drying in step one to granulation, and after granulation, subjecting the resultant to solvent extraction using organic solvents such as hexane, cyclohexane, n-heptane, petroleum ether, vegetable oil extraction solvent, ethyl acetate, butyl acetate and the like, and concentrating the resulted extract to 1/15 to 1/5 of the original solvent volume;

step three, adding methanol, ethanol, pentanol, butanol, isopropanol, and the like into the concentrated solution obtained after the treatment of step two for liquid-liquid extraction;

step four, separating the lower liquid after the treatment of step three, and adding activated carbon for stirring to decolorize; and step five, concentrating the decolorized liquid obtained after the treatment of step four, and deodorizing to obtain a cannabidiol-rich oil paste.

A preferred method for industrial extraction of cannabidiol is also provided by the present application, which is characterized by the following steps:

step one, crushing the hemp flowers and leaves to 15-25 mesh and subjecting the resultant to heating and tossing or drying treatment at 125-135° C.;

step two, subjecting the hemp flowers and leaves after the treatment of drying in step one to granulation, and after granulation, subjecting the resultant to solvent extraction using hexane, petroleum ether, or vegetable oil extraction solvent, the mass/volume ratio (g/mL) of the hemp flowers and leaves to the extraction solvent is 1:4 to 1:8; the extraction solution is concentrated to 1/12-1/8 of the original solvent volume;

step three, adding 60%-75% of methanol, ethanol, pentanol, butanol or isopropanol into the concentrated solution obtained from step two for liquid-liquid extraction, with a volume ratio of the concentrated solution to the liquid-liquid extraction solvent of 1:2 to 1:6;

step four, separating the lower liquid after the treatment in step three, and adding activated carbon for stirring to decolorize; and step five, concentrating the decolorized liquid obtained from step four, and deodorizing to obtain a cannabidiol-rich oil paste.

A preferred method for industrial extraction of cannabidiol is also provided by the present application, which is characterized by the following steps:

step one, crushing the hemp flowers and leaves to 20 mesh and subjecting the resultant to heating and tossing or drying treatment at 130° C.;

step two, subjecting the hemp flowers and leaves after the treatment of drying in step one to granulation, and after granulation, subjecting the resultant to solvent extraction using hexane, petroleum ether or vegetable oil extraction solvent, the mass/volume ratio (g/mL) of the hemp flowers and leaves to the extraction solvent is 1:4 to 1:8; the extraction solution is concentrated to 1/10 of the original solvent volume;

step three, adding 60%-75% of methanol or ethanol into the concentrated solution obtained after the treatment of step two for liquid-liquid extraction, with a volume ratio of the concentrated solution to the liquid-liquid extraction solvent of 1:2 to 1:6, after addition, stirring the resultant for 10 min to 30 min and left standing for 60 min to 120 min;

step four, separating the lower liquid after the treatment of step three, and adding woody porous activated carbon for stirring to decolorize for 5 min to 10 min; and step five, concentrating the decolorized liquid obtained after the treatment of step four, and deodorizing to obtain a cannabidiol-rich oil paste.

Granulation technology is used in step two of the present invention, so that the solvent in the leaching process to fully contact the material, greatly improving the extraction rate, while improving the filtration rate of the material liquid. Conventional granulation methods are used for granulation. The vegetable oil extraction solvent in the extraction solvents is an aliphatic hydrocarbon-based solvent, mainly hexane, pentane, butane, propane and the mixtures thereof, especially the solvent of hexane mixture; the vegetable oil extraction solvent mentioned in the present invention refers to the vegetable oil soluble extraction solvent that meets the current national standards of China.

The step of extraction in step two of the present invention can leave the wax and tetrahydrocannabinol in the original extraction solution and cannabidiol to be reverse extracted into the extractant.

The proportion of activated carbon added in step four of the present invention is 0.1%-3%, which can remove the color of impurities, improve the purity of cannabidiol and improve the appearance of the product; the activated carbon is preferably woody porous activated carbon, which can be decolorized for 5 to 10 minutes to achieve the effect, and in the case of decolorization, impurities can also be treated to improve the purity of cannabidiol in the extract.

SPECIFIC MODES FOR CARRYING OUT THE EMBODIMENTS

The following Examples are intended to further illustrate the present invention, but are not intended to limit the scope of the present invention in any way. Any changes or substitutions based on the teachings of the present invention belong to the scope of protection of the present invention.

Example 1

Step one, 230 g of sun-dried hemp flowers and leaves were crushed to 20 mesh and subjected to heating and drying in an oven at 130° C. for 1 h;

step two, 200 g of hemp flowers and leaves obtained from step one were granulated after adding 1% of water to form solid particles, extracted with 5 times the volume in proportion of petroleum ether 1000 ml solvent, and the extract solution was filtered and concentrated to 100 ml remained;

step three, 300 ml of 70% of methanol solvent was added into the concentrated solution obtained from step two for liquid-liquid extraction;

step four, the methanol layer obtained after the treatment in step three was separated and 3 g of woody activated carbon was added, stirred for 10 min and filtered to obtain a clear and transparent stock solution; and step five, the methanol decolorized solution obtained from step four was concentrated and deodorized to obtain 16 g of cannabidiol-rich oil paste.

Example 2

Step one, 460 g of hemp flowers and leaves were crushed to 20 mesh and subjected to heating and drying in an oven at 130° C. for 1 hour;

step two, 400 g of hemp flowers and leaves after drying in step one were granulated after adding 1.5% of water to form solid particles, extracted with 3200 ml of vegetable oil extraction solvent, and the extract solution was filtered and concentrated to 320 ml remained;

step three, 1280 ml of 75% of ethanol solvent was added into the concentrated solution obtained after the treatment of step two for liquid-liquid extraction;

step four, the ethanol layer obtained after the treatment of step three was separated and 25.6 g of woody activated carbon was added thereto, filtered after stirring for 5 min to obtain a clear and transparent stock solution; and step five, the ethanol decolorized solution obtained after the treatment of step four was concentrated and deodorized to obtain 30 g of cannabidiol-rich oil paste.

Example 3

Step one, 120 g of sun-dried hemp flowers and leaves were crushed to 20 mesh and subjected to heating and drying in an oven at 130° C. for 1 hour;

step two, 100 g of hemp flowers and leaves obtained from step one were granulated after adding 1% of water to form solid particles, extracted with 5 times the volume in proportion of hexane 500 ml solvent, and the extract solution was filtered and concentrated to 60 ml remained;

step three, 240 ml of 72% of isopropanol solvent was added into the concentrated solution obtained after the treatment of step two for liquid-liquid extraction;

step four, the isopropanol layer obtained after the treatment in step three was separated and 3 g of woody activated carbon was added, stirred for 10 min and filtered to obtain a clear and transparent stock solution; and step five, the isopropanol decolorized solution obtained after the treatment of step four was concentrated and deodorized to obtain 7.6 g of cannabidiol-rich oil paste.

Comparative Example 1

Step one, 230 g of sun-dried hemp flowers and leaves were crushed to 20 mesh and subjected to heating and drying in an oven at 130° C. for 1 hour;

step two, 200 g of hemp flowers and leaves obtained from step one were granulated after adding 1% of water to form solid particles, extracted with 5 times the volume in proportion of 70% of methanol 1000 ml solvent, and the extract solution was filtered and concentrated to 100 ml remained;

step three, 300 ml of petroleum ether solvent was added into the concentrated solution obtained after the treatment of step two for liquid-liquid extraction;

step four, the petroleum ether layer obtained after treatment of step three was separated and 3 g of woody activated carbon was added, filtered after stirring for 10 min to obtain a clear and transparent stock solution; and step five, the decolorized liquid obtained after the treatment of step four was concentrated and deodorized to obtain 18 g of cannabidiol-rich oil paste.

Comparative Example 2

Step one, 120 g of sun-dried hemp flowers and leaves were crushed to 20 mesh and subjected to heating and drying in an oven at 130° C. for 1 hour;

step two, 100 g of hemp flowers and leaves obtained from step one were granulated after adding 1% of water to form solid particles, extracted with 5 times the volume in proportion of hexane 500 ml solvent, and the extract solution was filtered and concentrated to 60 ml remained;

step three, 3 g of woody activated carbon was added into the concentrated solution obtained after the treatment of step two, and after stirring for 10 min, being filtered;

step four, the decolorized solution obtained after the treatment of step three was concentrated and deodorized to obtain 8.5 g of cannabidiol-rich oil paste.

Effect of the extraction processes on the content of cannabidiol and tetrahydrocannabinol in the extracted product:

The content of the cannabidiol oil paste described in the Examples and the Comparative Examples was determined and the content data are shown in the following table.

| Sample | Content of cannabidiol/% | Content of tetrahydrocannabinol/% |
|---|---|---|
| Example 1 | 42.0 | 2.41 |
| Example 2 | 43.0 | 2.50 |
| Example 3 | 42.2 | 2.42 |
| Comparative Example 1 | 18.6 | 8.15 |
| Comparative Example 2 | 17.9 | 8.26 |

It can be seen from the Table above that the cannabidiol in the form of oil paste obtained from the Example has high cannabidiol content and low tetrahydrocannabinol content, while the cannabidiol in the form of oil paste obtained from the Comparative Example has low cannabidiol content and high tetrahydrocannabinol content, indicating that the adjustment of the extraction solvent and extractant of the present application can greatly remove impurities from the extract and increase the cannabidiol content, while also removing some of the tetrahydrocannabinol, providing high-quality raw materials for the subsequent further refinement of cannabidiol.

INDUSTRIAL APPLICABILITY

The present invention provides an industrial extraction method of cannabidiol. The present invention aims to resolve the problems of difficulty in wax removal, low extraction rate of cannabidiol, and excessively high content of tetrahydrocannabinol during extraction using conventional solvents in the prior art. The extraction method employs raw material pretreatment, granulation, extraction, liquid-liquid extraction, decolorization, concentration, and other processes, such that wax removal from an extracted liquid is improved, the purity of a crude cannabidiol oil can be increased to 60%, and 40% of tetrahydrocannabinol can be removed. The method has high extraction yields and low costs, and can be implemented in large-scale industrial production, which has good economic value and application prospects.

What is claimed is:

1. A method for industrial extraction of cannabidiol, characterized by comprising the following steps:

step one, crushing hemp flowers and leaves and subjecting the crushed hemp flowers and leaves to heating and tossing or drying treatment at 100-150° C.;

step two, subjecting the crushed hemp flowers and leaves after the drying treatment in step one to solvent extraction, and concentrating the resultant extract solution to a certain amount remaining;

step three, adding other solvents into the concentrated solution obtained after treatment in step two for liquid-liquid extraction;

step four, separating the resultant lower liquid after the treatment in step three, and adding activated carbon for stirring to decolorize; and step five, concentrating the decolorized liquid obtained after treatment in step four, and deodorizing to obtain a cannabidiol-rich oil paste.

2. The method for industrial extraction of cannabidiol according to claim 1, wherein, the extraction solvent in step two is an organic solvent selected from the group consisting of hexane, cyclohexane, n-heptane, petroleum ether, vegetable oil extraction solvent, ethyl acetate, butyl acetate and the like, and the mass/volume ratio (g/mL) of the crushed hemp flowers and leaves to the extraction solvent is 1:4 to 1:8.

3. The method for industrial extraction of cannabidiol according to claim 2, wherein, the extraction solvent in step two is selected from the group consisting of hexane, petroleum ether and vegetable oil extraction solvent; and the extraction solution is concentrated to 1/5 to 1/15 of a volume of the original extraction solvent.

4. The method for industrial extraction of cannabidiol according to claim 1, wherein, the liquid-liquid extraction solvent used in step three is a solvent selected from the group consisting of methanol, ethanol, pentanol, butanol, isopropanol and the like; a volume ratio of the concentrated solution to the liquid-liquid extraction solvent is 1:2 to 1:6; after the liquid-liquid extraction solvent is added, the obtained solution is stirred for 10 min to 30 min and left standing for 60 min to 120 min, so that two phases of the solvent are completely separated.

5. The method for industrial extraction of cannabidiol according to claim 4, wherein, the extractant used in step three is selected from the group consisting of 60%-75% of methanol, ethanol, pentanol, butanol and isopropanol.

6. The method for industrial extraction of cannabidiol according to claim 4, wherein, the extractant used in step three is selected from the group consisting of 60%-75% of methanol and ethanol.

7. The method for industrial extraction of cannabidiol according to claim 1, wherein, the amount of the activated carbon added in step four is 0.1%-3% (g/ml) of the lower liquid.

8. The method for industrial extraction of cannabidiol according to claim 1, wherein, the crushed hemp flowers and leaves in step two are granulated and then extracted.

9. The method for industrial extraction of cannabidiol according to claim 1, wherein, the activated carbon in step four is woody porous activated carbon, and a treatment time for step four is 5 to 10 minutes.

10. The method for industrial extraction of cannabidiol according to claim 2, wherein, the liquid-liquid extraction solvent used in step three is a solvent selected from the group consisting of methanol, ethanol, pentanol, butanol, isopropanol and the like; the volume ratio of the concentrated solution to the liquid-liquid extraction solvent is 1:2 to 1:6; after the liquid-liquid extraction solvent is added, the obtained solution is stirred for 10 min to 30 min and left standing for 60 min to 120 min, so that the two phases of the solvent are completely separated.

11. The method for industrial extraction of cannabidiol according to claim 3, wherein, the liquid-liquid extraction solvent used in step three is a solvent selected from the group consisting of methanol, ethanol, pentanol, butanol, isopropanol and the like; the volume ratio of the concentrated solution to the liquid-liquid extraction solvent is 1:2 to 1:6; after the liquid-liquid extraction solvent is added, the obtained solution is stirred for 10 min to 30 min and left standing for 60 min to 120 min, so that the two phases of the solvent are completely separated.

12. The method for industrial extraction of cannabidiol according to claim 5, wherein, the extractant used in step three is selected from the group consisting of 60%-75% of methanol and ethanol.

13. The method for industrial extraction of cannabidiol according to claim 2, wherein, the amount of the activated carbon added in step four is 0.1%-3% (g/ml) of the lower liquid.

14. The method for industrial extraction of cannabidiol according to claim 3, wherein, the amount of the activated carbon added in step four is 0.1%-3% (g/ml) of the lower liquid.

15. The method for industrial extraction of cannabidiol according to claim 4, wherein, the amount of the activated carbon added in step four is 0.1%-3% (g/ml) of the lower liquid.

16. The method for industrial extraction of cannabidiol according to claim 5, wherein, the amount of the activated carbon added in step four is 0.1%-3% (g/ml) of the lower liquid.

17. The method for industrial extraction of cannabidiol according to claim 6, wherein, the amount of the activated carbon added in step four is 0.1%-3% (g/ml) of the lower liquid.

18. The method for industrial extraction of cannabidiol according to claim 2, wherein, the crushed hemp flowers and leaves in step two are granulated and then extracted.

19. The method for industrial extraction of cannabidiol according to claim 3, wherein, the crushed hemp flowers and leaves in step two are granulated and then extracted.

20. The method for industrial extraction of cannabidiol according to claim 4, wherein, the crushed hemp flowers and leaves in step two are granulated and then extracted.

* * * * *